United States Patent [19]
Lawrence

[11] Patent Number: 5,288,459
[45] Date of Patent: Feb. 22, 1994

[54] PROCESS FOR IMPROVING THE SHELF LIFE OF WHOLE BLOOD

[75] Inventor: Joseph L. Lawrence, New York, N.Y.

[73] Assignee: Biolectron, Inc., Hackensack, N.J.

[21] Appl. No.: 74,003

[22] Filed: Jun. 8, 1993

Related U.S. Application Data

[63] Continuation of Ser. No. 221,291, Jul. 19, 1988, abandoned.

[51] Int. Cl.$^5$ .............................................. A61L 2/02
[52] U.S. Cl. ....................................... 422/22; 422/40; 422/41; 435/2
[58] Field of Search ................... 422/22, 40, 41; 435/2

[56] References Cited

U.S. PATENT DOCUMENTS

| 3,706,631 | 12/1972 | Falk | 422/21 X |
| 4,250,139 | 2/1981 | Luck et al. | 422/21 |
| 4,695,472 | 9/1987 | Dunn et al. | 426/237 |

OTHER PUBLICATIONS

Kinosita, Jr. et al., *Nature* 268(4) (Aug. 1977).

Primary Examiner—Jill A. Johnston
Attorney, Agent, or Firm—Schweitzer Cornman & Gross

[57] ABSTRACT

A process is disclosed wherein whole blood or a blood fraction, such as platelets or leukocytes are stored within a modulated electrical field, such as a capacitive field, to extend the shelf life of the blood or fraction.

6 Claims, 5 Drawing Sheets

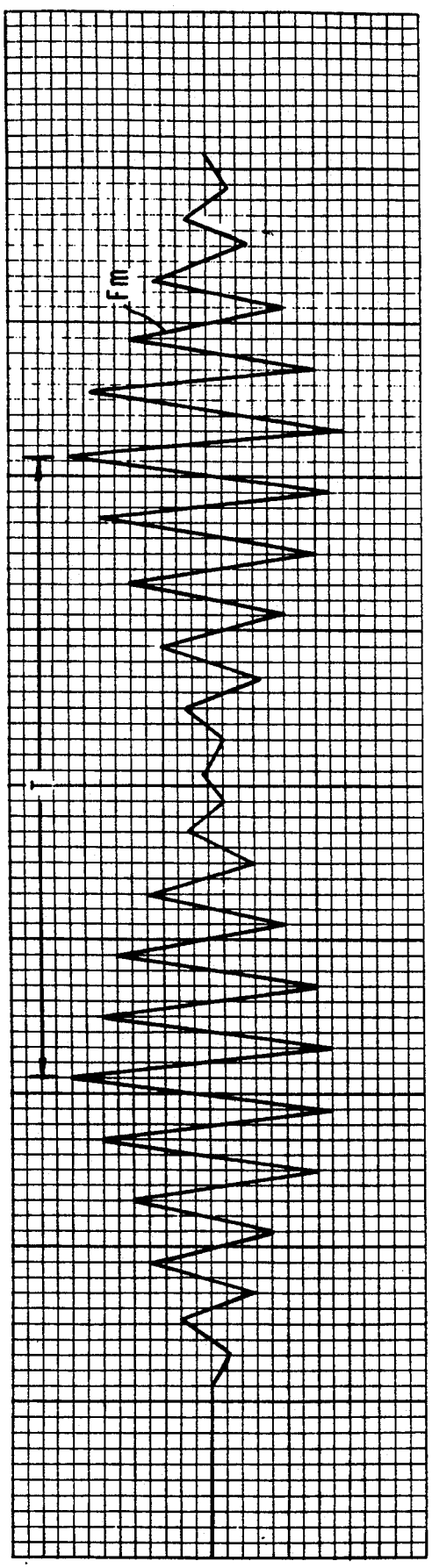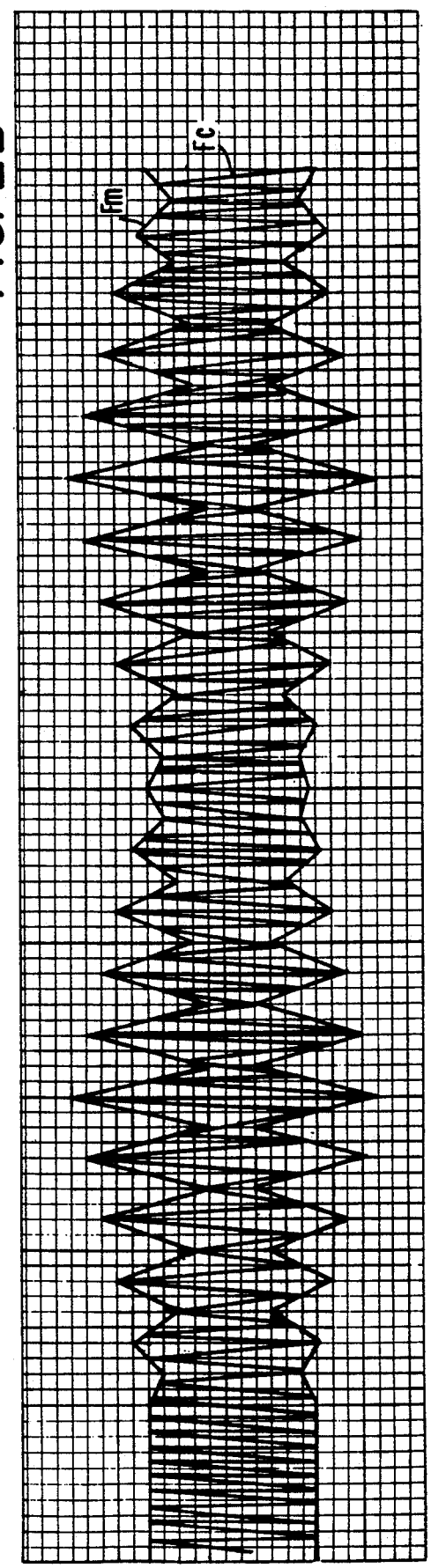

PROCESS FOR IMPROVING THE SHELF LIFE OF WHOLE BLOOD

This is a continuing application of U.S. Ser. No. 221,291 filed on Jul. 19, 1988, now abandoned.

FIELD OF THE INVENTION

The present invention relates to a process for increasing or extending the shelf life and quality of whole blood and of blood fractions, more particularly to a process for increasing or extending the shelf life of blood and fractions by exposing whole blood or a blood fraction to an electrical field.

BACKGROUND OF THE INVENTION

Blood is the medium which carries everything needed by ever every cell in the body. The shelf life of most blood fractions is measured within a span of only a few days. Therefore, it is highly desirable to find methods by which the shelf life and quality of whole blood and of blood fractions especially of platelets, leukocytes and red cells can be extended.

As used herein, reference to "quality" of whole blood or blood fractions treated in accordance with the present invention means that at the limits of the normal shelf life of like but untreated blood or fraction, the treated blood or fraction better retains the inherent components of the individual cells for a layer time to support normal and necessary physiological functions.

The various component fractions of the blood tissue are of cellular and fluid (plasma) types. Plasma comprises about 60% by vol. of whole blood and the cells comprise about 40% vol. The cellular components include erythrocytes (red blood cells), platelets, and leukocytes (white blood cells). Leukocytes comprise granulocytes (about 55% vol.), lymphocytes (about 40% vol.) and monocytes (about 5% vol.). Granulocytes have the shortest shelf life. The shelf life of lymphocytes and monocytes is somewhat better. The fluid components of blood include those carbohydrates, lipids, salt, minerals, and proteins which contain albumins, globulins, antibodies, and enzymes. The differing fractions can be used for various purposes and, therefore, the same unit of whole blood can yield components which can each find separate applications.

Whole blood is most often fractionated, because its fractions have different shelf lives and one or more fractions in whole blood which lose their viability may contaminate the rest. Furthermore, red cells will retain their shelf life for relatively long periods in the frozen state. Other blood fractions cannot tolerate freezing. The improvement of shelf life is most important for platelets and to a lesser extent for leukocytes. Platelets are in great demand, and extending their shelf life is of great importance. The platelet fraction, or platelets are given to patients in hemorrhagic disorders. Their principal function is to patch small defects in the endothelial lining of blood vessels and to limit hemorrhage by promoting local coagulation of the blood. Currently platelets have an in vitro shelf life of about five days.

Lymphocytes are comprised of two major subclasses, T-lymphocytes and B-lymphocytes. Their primary function is to regulate the immune system to produce antibodies. The antibodies can be effective against bacteria, viruses, or particulate matter. AIDS and AIDS related syndromes are a direct result of improper functioning of T & B cell systems. Therefore, any product which has a positive effect on regulating their shelf life to preserve them for longer periods of usefulness will have a beneficial effect also upon combating AIDS.

White blood cells, particularly T-cells are also used in the biotechnology industry to produce monoclonal antibodies. Such antibodies have an ever increasing application in therapy and have achieved some advances as diagnostic agents, such as in viral or bacterial diagnostic kits and to enhance the development and yield of the antiviral agents.

Platelets generally become unstable after about five days, and even during this period they have to be agitated or gently rotated to keep them from clumping. The number of blood donors has been declining primarily due to the AIDS scare and there appears to be a constant shortage in the available amount of platelets. For example, between 1984 and 1985 the total number of plateletpheresis procedures increased by over 24%. During the same period the total number of blood transfers increased only by merely 3%. This indicates that platelet requirements are significantly increased over the total number of transfusions and this suggests an increase in the proportion of clinical usage of platelets. An increase in shelf life of about two days of the platelets would increase the supply by about 40%. Such an extended supply would mean that the increased present need for platelets would be achieved by fewer blood donors. Hence, the most important need is for the extension of the shelf life of the platelets.

BRIEF DESCRIPTION OF THE INVENTION

It was discovered that the shelf life of whole blood, unfractionated white blood cells (sedimented buffy coat), and of platelets can be improved by storing in vitro within an effective electrical field.

Although most of the findings were obtained by exposure to a capacitive electrical field, and it was also found that increasing the power of the field beyond a certain value does not bring about any improvement or may even result in a decline of shelf life, the term "effective electrical field" as used throughout the specification and the claims is intended to cover all varieties of electrical fields and all intensities, frequencies and wave forms of the field which will bring about improvement of the shelf life of the blood fraction. The nature and magnitude and other parameters of the field for most effective use can be determined by routine experimentation, such as is also illustrated herein.

The blood fraction to be treated in accordance with the present invention should have a sufficiently high concentration (i.e. cell or platelet count) for the process of the present invention to be effective. Accordingly, the term "effective concentration" as applied to a blood fraction, as used throughout the specification and claims, denotes a concentration that is above the minimum concentration level at which the present process becomes effective. Such minimum concentration levels can be determined by routine experimentation.

The application of electrical fields to the musculoskeletal system is well known from the use of electrical stimulation of bones for accelerating and enabling the healing of problem fractures. For a general description of these uses and a variety of electrical fields and parameters applied in such uses reference is made to a book by J. Black: Electrical Stimulation—It's Growth, Repair and Remodeling of the Musculoskeletal System; Praeger Publ., 1939.

DESCRIPTION OF THE DRAWING

The invention is described with reference being made to the drawing, wherein

FIG. 2a is an illustration of a composite audio frequency wave form of an electric field;

FIG. 2b is an illustration of an amplitude modulated embodiment of the wave form of FIG. 3a;

DETAILED DESCRIPTION OF THE INVENTION

A series of experiments were carried out to study the effect of effective electrical fields on the in vitro preservation of human blood cells. These experiments were carried out with capacitively coupled electrical current.

Figure 1:
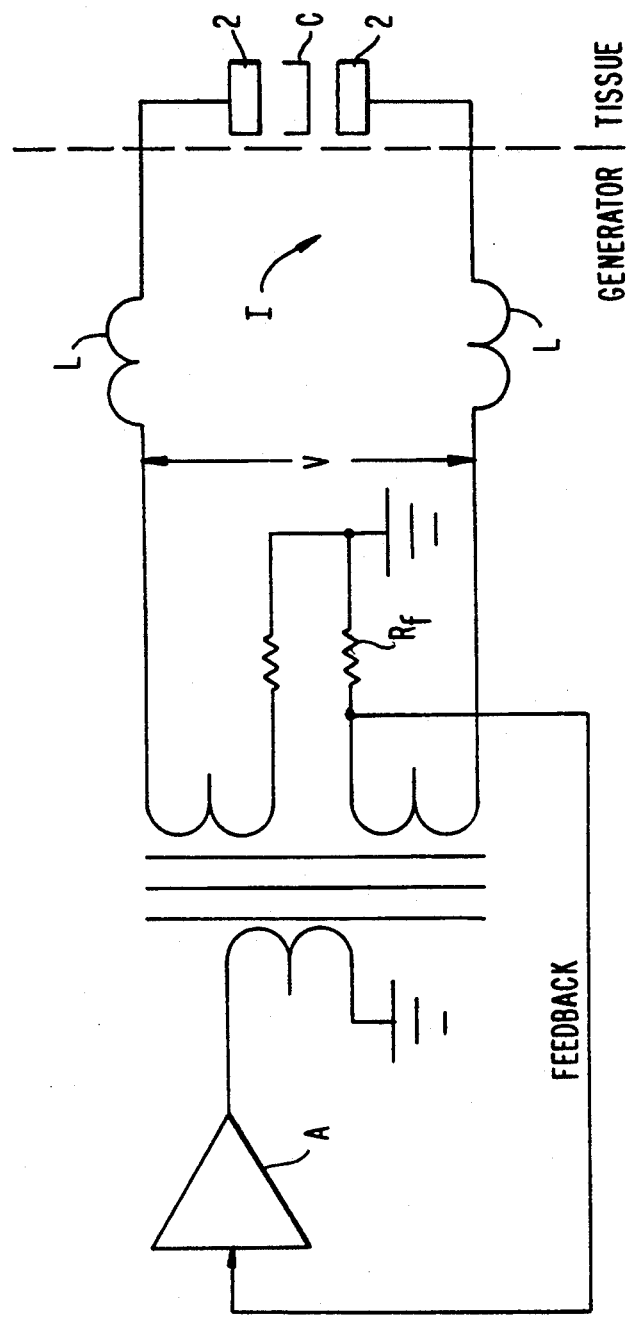
FIG. 1 is a general schematic illustration of the apparatus employed in the in vitro experiments.

An example of producing an effective electrical field is by means of the circuitry and coupling methods shown in FIG. 1. The electrical energy is transmitted from the generator to the bag containing blood or fractions thereof by means of a series resonance L-C circuit in which the capacitance of the blood tissue (C) constitutes one of the elements of the L-C circuit. A fixed high Q inductor or inductors L inside the generator comprise the other elements of the L-C circuit. The output of the generator is coupled through this inductor by means of metal plates (electrodes) 2 to the vessel containing the blood or fraction (C). The capacitance value of the blood or fraction may change when subjected to an electric field, but the value of the fixed inductor remains the same. Therefore, the series resonance conditions can be maintained only if the generated frequency is caused to change in proper proportion to the change in capacitance value of the blood or fractions (C). The resonance circuit composed of the blood or fractions and the fixed inductor function together as the frequency determining network for the carrier oscillator of the generator.

When series resonance occurs in the circuit of FIG. 1, the output voltage V of the carrier and its output current I are in phase and the current is at its maximum level. The current is sensed by a small feedback resistor $R_f$ in series with the resonance circuit and the resulting voltage developed across it is fed back into the input amplifier A. Since this feedback voltage is in phase with the output voltage, and the feedback is arranged to be positive, the circuit will maintain oscillation at the frequency determined by the inductors and the capacitance of blood or fraction.

Due to the characteristics of the circuit of FIG. 1, the voltage across the blood or fraction is Q times larger than than the generator output voltage. Q is the quality factor of the circuit. Since the capacitive voltage is 90 degrees out of phase with the current, it does not contribute to power dissipation. The series resonance coupling allows the transmission of a relatively high current into the blood or fraction at a relatively low generator output voltage.

The wave form which is employed may have an effect on the desired result. In FIG. 2a a composite audio frequency wave form is shown, which is generated by linearly multiplying a swept audio frequency signal by a repetitive isosceles triangle wave form. A carrier ($f_c$) is amplitude modulated by this composite audio frequency wave form of FIG. 2a to produce the wave form shown in FIG. 2b. The signal varies linearly in amplitude from zero to maximum at intervals T of the triangle wave, as shown in FIG. 2a. The degree of modulation is proportional to the ratio of amplitude of the modulating signal to the amplitude of the carrier.

In actual use the carrier amplitude is kept to the predetermined constant level which can be selected to be optimum for any particular use. Thus, the output wave form of the carrier depends completely on the shape and amplitude of the modulating signal. The carrier is unmodulated when the amplitude of the modulation signal is zero, and is maximum when the the modulating signal amplitude is at a maximum. Adjustment of the maximum level of the modulated signal can be used to set the actual percentage of modulation at maximum, to any desired level. The modulating period T can also be preselected for optimum specific applications.

Typically, parameters for the output wave form can be for the period T=1 second; modulating frequency $f_m$=50–400 Hz, each 3 minutes; carrier frequency $f_c$=75 KHz; and modulation index=50% (the modulation index is the ratio of the amplitude of the modulated signal to the amplitude of the carrier).

For additional explanation of the electronic circuitry and its operation reference is made hereby to U.S. Pat. No. 3,563,246.

Studies were carried out to determine the effects of capacitive coupled electric current on the in vitro preservation of human blood cells. All blood studied was freshly obtained from volunteer donors. Leukocytes were obtained by concentration with dextran from buffy coat white cells isolated by centrifugation of ACD anticoagulated whole blood. Platelets were obtained from platelet rich plasma and the red cells were studied in whole blood without prior isolation. Cell suspensions in plasma were placed in plastic 150 ml Fenwal transfer packs and then the packs were used as the dielectric in an electric stimulator employing the wave form of FIG. 2b. An electrical field generating stimulator sold by Biolectron Inc. under the trade designation BBS-4, was used in all experiments. The current was applied for period of up to 28 days for given current and modulation. Aliquots were removed at intervals for enumeration of cells, and determination of hematologic parameters appropriate to the cell type.

The main data for leukocytes was the white cell differential count, the in vitro viability as assessed in cytoplasmic and nuclear membranes, and cell volumes.

For platelets, counts, volumes and acidities were measured and for red cells counts, hemoglobin, hematocrits, and volumes were taken. These data were obtained with a fluorescence microscope, a Coulter SPLUS-IV, diff. counter with histrogram differential, counter, a Coulter ZH volume counter and channelyzer, and a blood gas analyzer from Instrumentation Laboratories. The data supports the conclusion that stimulation in an electrical field increases the in vitro life span of whole blood, white cells and platelets, and to a somewhat lesser extent that of red cells.

The shelf life of whole blood was extended by about 30% as determined by the ATP level of red cells.

White cells studies in repeat experiments clearly showed better preservation in the range of 6–14 days. Both the cell count and percentage of viable cells were higher than in the case of controls that were not stimulated in the electrical field. Excitation in a 2 ma and a 4 ma field gave similar results, however, application of higher current was shown to be so detrimental that at 6 ma, the shelf life extending effect was eliminated.

In the case of white cells about 10% of the cells remained viable at about 12-13 days.

Also about 25% increase in red count is obtained with an increase in hematocrit in the cells stimulated by electrical field. At 4 ma for 20 days a consistently higher red cell count was supported by higher hemoglobin and hematocrit values.

The most dramatic results were obtained with blood platelets, wherein a better maintenance of lower volume and higher pH is indicative of and consistent with higher viability. The improved platelet shelf life using electrical field exposure was further demonstrated when the effect failed to manifest itself. It was discovered that the platelet count of the sample was too low. Upon an increase of the count to higher, effective levels, the shelf life increasing effect of the electrical field could be reproduced.

The invention is further illustrated by way of the following specific examples.

EXAMPLE 1

50 milliliters of 2% dextran was added to an equal volume of ACD anticoagulated buffy coat blood. The bag was inverted several times to mix the suspension. The bag was suspended upside down and allowed to settle for 18-20 minutes until a clear interface was formed between the leukocyte rich plasma (LRP) and the red cells. The red cells were drained and discarded. The LRP was centrifuged at 1,000 r.p.m. for 10 minutes at 22° C. in a Sorvall RC3B centrifuge. The supernatant was expressed and the packed leukocytes were suspended in 100 ml of a 1:1 plasma:PBS-glucose medium.

Figure 3:
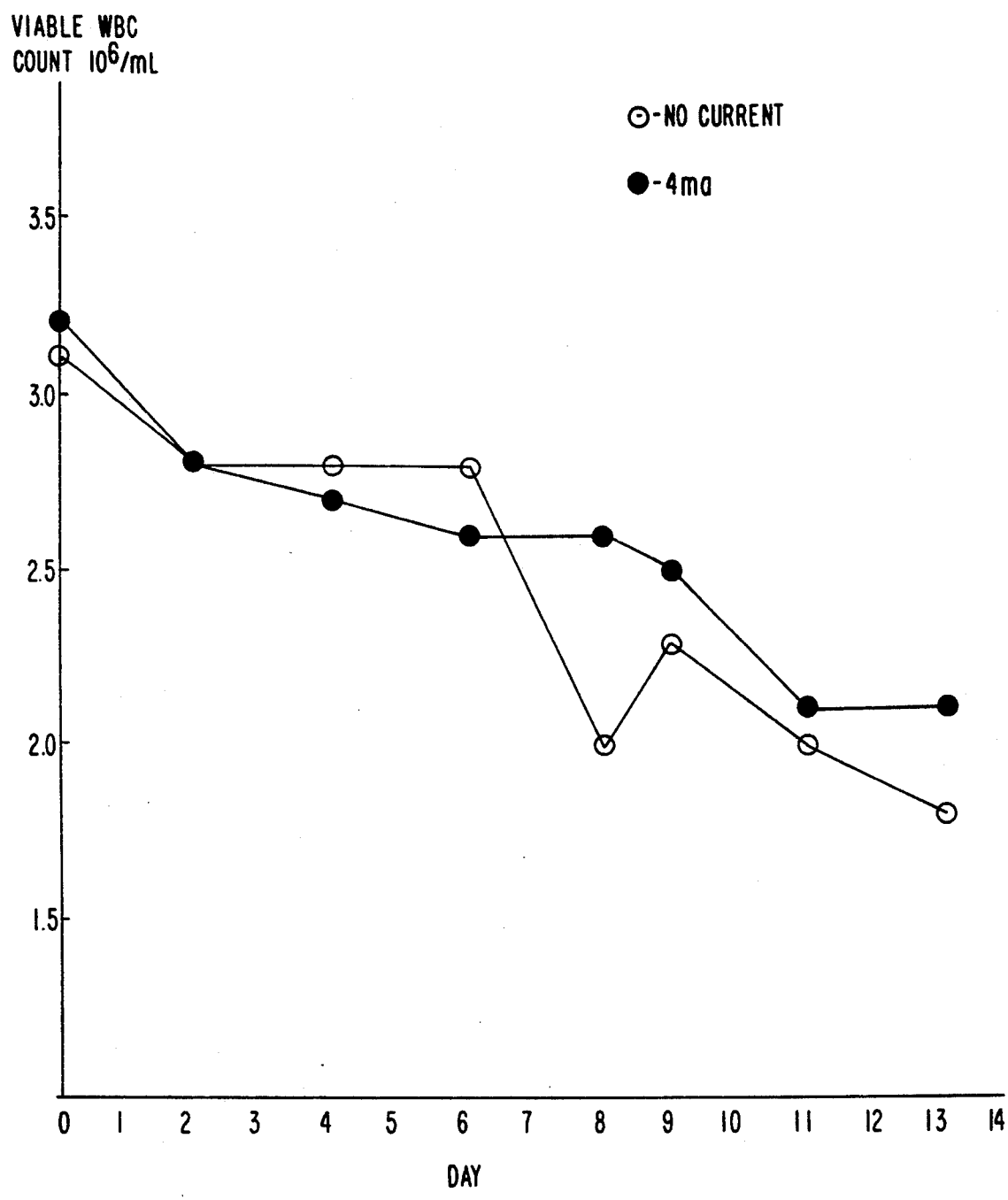
FIG. 3 is a diagram showing the effect of electrical field on white blood cells.

50 milliliters of the leukocyte suspension was placed into a 150 ml Transfer Pack Unit made by Fenwal Laboratories, USA. Two samples were prepared and placed into separate cell bag holders made by Biolectron Inc. One bag had a current of 4 ma applied to it with 50% oscillation and the other bag was used as a control without current. The results are shown in FIG. 3.

EXAMPLE 2

Figure 4:
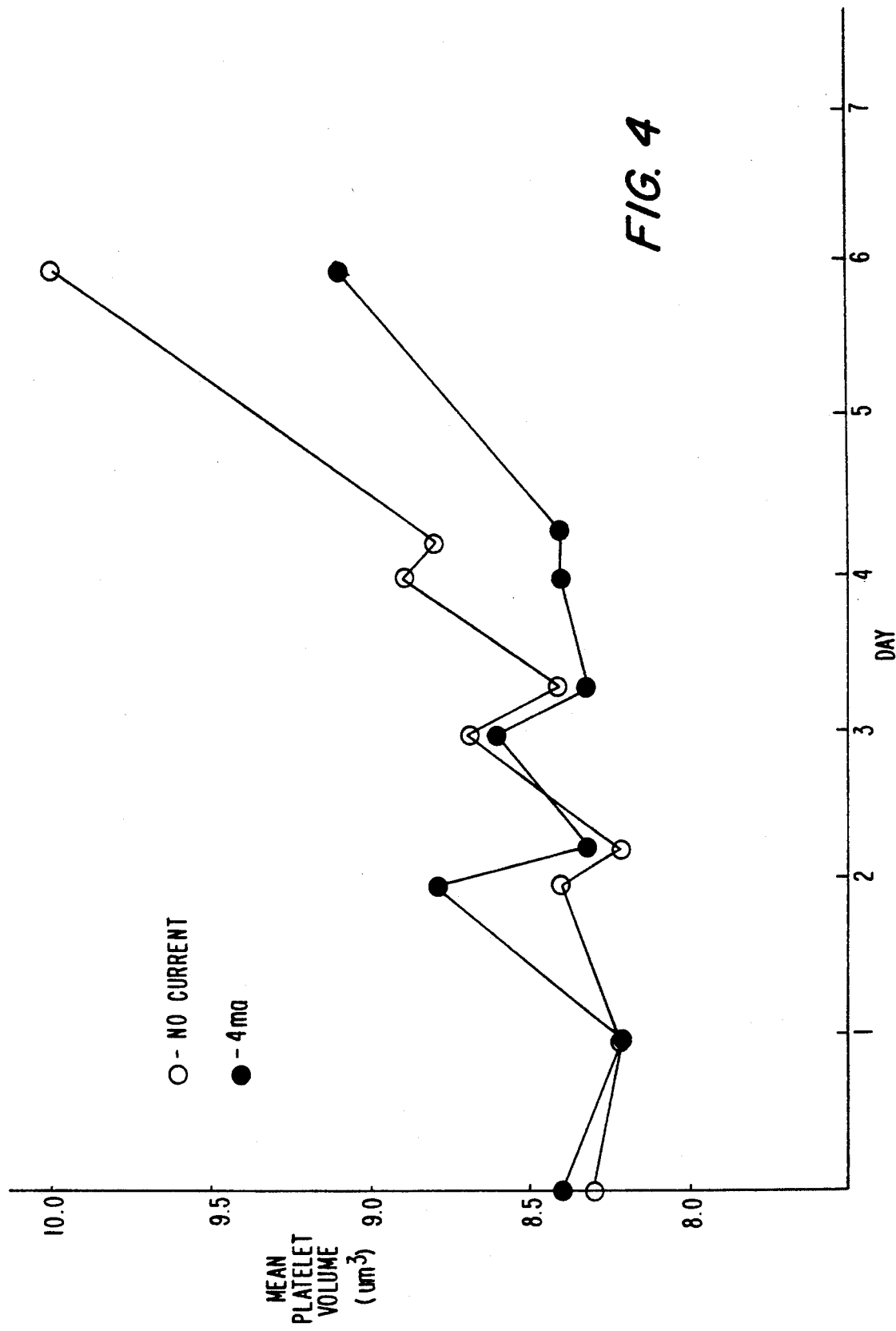
FIG. 4 is a diagram showing the effect of electrical field on platelets.

120 milliliters of platelets were obtained by centrifuging a unit of ACD anticoagulated whole blood and by expressing the plasma into a 300 ml satellite bag. ml of the platelet rich plasma (PRP) was expressed into a 150 ml Transfer Pack Unit made by Fenwall Laboratories. Two samples were prepared and placed into separate cell bag holders made by Biolectron Inc. One bag had a current of 4 ma applied to it with 50% oscillation and the other bag was used as a control without any current. The results are shown in FIG. 4.

EXAMPLE 3

1 unit (450 ml) ACD anticoagulated whole blood was centrifuged at 2500 r.p.m. for 3 minutes. The platelet rich plasma (PRP) was expressed into a 300 ml satellite bag. The PRP was then centrifuged at 3500 r.p.m. for 5 minutes to pellet the platelets. Approximately 100 ml of the plasma supernatant was removed and the remaining platelets were kneaded until they were resuspended.

Figure 5:
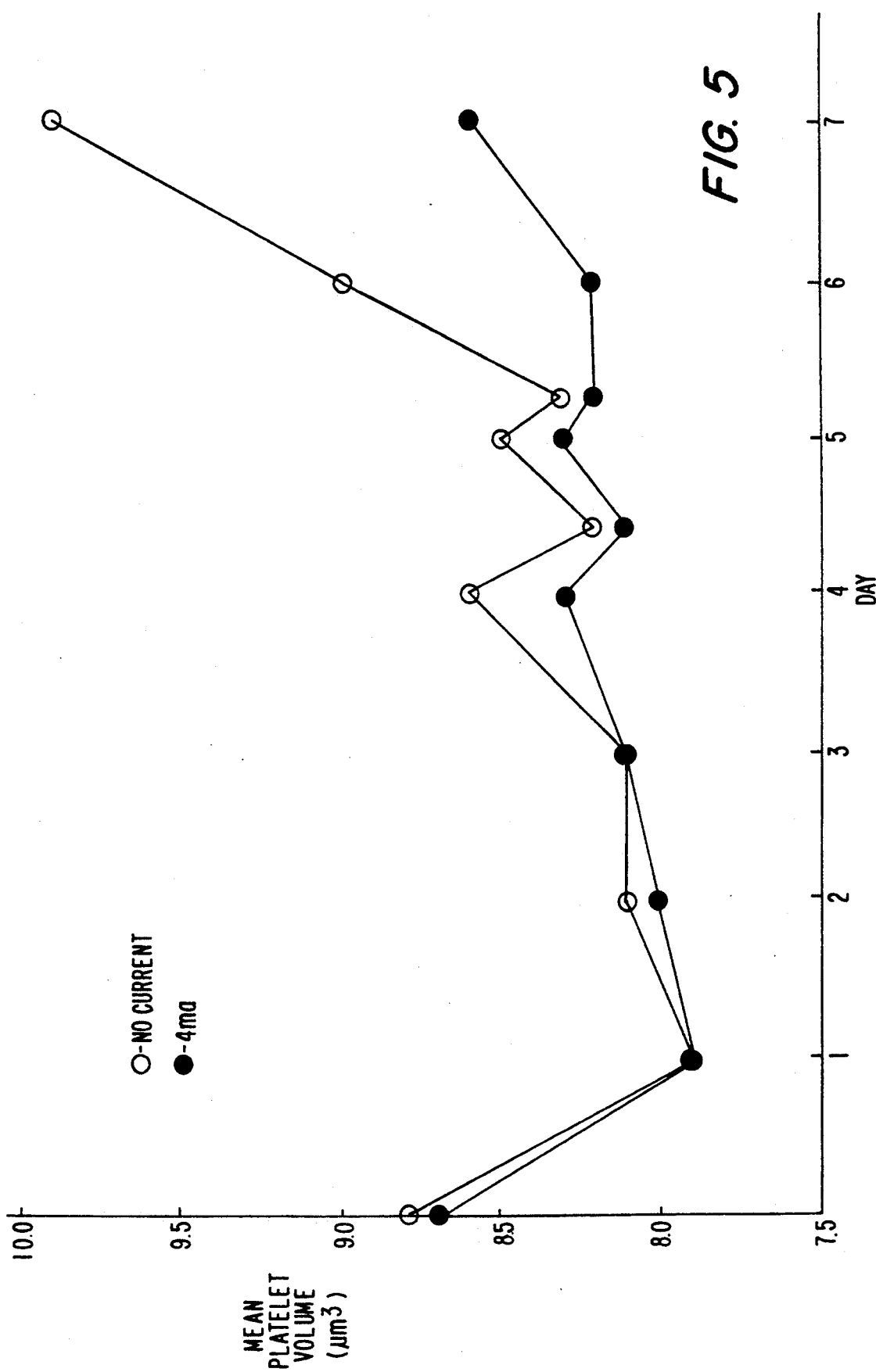
FIG. 5 is another diagram showing the effect of electrical field on platelets.

50 ml of the resuspended PRP was placed into a 150 ml Transfer Pack Unit made by Fenwall Laboratories. Two samples were prepared and placed into separate cell bag holders made by Biolectron Inc. One bag had a current of 4 ma applied to it with 50% oscillation and the other bag was used as a control without any current. The results are shown in FIG. 5.

I claim:

1. A process for extending the shelf life and quality of whole blood and of blood fractions, which comprises storing a blood or blood fraction within a modulated, alternating current capacitive electrical field.

2. The process of claim 1, wherein the modulated capacative alternating current electrical field has the wave form shown in FIG. 2b.

3. The process of claim 1, wherein the blood fraction comprises platelets.

4. The process of claim 1, wherein the blood fraction comprises leukocytes.

5. The process of claim 1, wherein the blood fraction comprises red cells.

6. The process of claim 1, wherein whole blood comprises the liquid components plasma and serum, and solid components which are formed cellular elements.

* * * * *